US009808585B2

(12) United States Patent
Wendland et al.

(10) Patent No.: US 9,808,585 B2
(45) Date of Patent: Nov. 7, 2017

(54) DRUG DELIVERY DEVICE WITH TAMPER-EVIDENT CLOSURE MEANS

(75) Inventors: Stefan Wendland, Frankfurt am Main (DE); Steffen Raab, Frankfurt am Main (DE); Peggy Rabe, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 430 days.

(21) Appl. No.: 14/002,177

(22) PCT Filed: Mar. 15, 2012

(86) PCT No.: PCT/EP2012/054536
§ 371 (c)(1),
(2), (4) Date: Aug. 29, 2013

(87) PCT Pub. No.: WO2012/123532
PCT Pub. Date: Sep. 20, 2012

(65) Prior Publication Data
US 2013/0338585 A1    Dec. 19, 2013

(30) Foreign Application Priority Data
Mar. 17, 2011   (EP) ..................................... 11158628

(51) Int. Cl.
*A61M 5/50*   (2006.01)
*A61M 5/24*   (2006.01)
(52) U.S. Cl.
CPC ............ *A61M 5/5086* (2013.01); *A61M 5/24* (2013.01); *A61M 5/50* (2013.01)

(58) Field of Classification Search
CPC ......... A61M 5/24; A61M 5/50; A61M 5/5086
See application file for complete search history.

(56) References Cited

U.S. PATENT DOCUMENTS

| 533,575 A | 2/1895 | Wilkens |
| 4,772,271 A | 9/1988 | Meyer et al. |

(Continued)

FOREIGN PATENT DOCUMENTS

| EP | 0937471 | 8/1999 |
| EP | 0937476 | 8/1999 |

(Continued)

OTHER PUBLICATIONS

International Search Report for Int. App. No. PCT/EP2012/054536, completed Oct. 29, 2012.

*Primary Examiner* — Imani Hayman
(74) *Attorney, Agent, or Firm* — McDonnell Boehnen Hulbert & Berghoff LLP

(57) ABSTRACT

A drug delivery device for administering a dose of a medicament by way of injection is disclosed, the device including a housing to receive a cartridge at least partially filled with a medicament and being sealed with a piston slidably disposed therein, a drive mechanism having a piston rod to be displaced in a distal direction to operably engage with the piston of the cartridge, a dose button operably engaged with the drive mechanism for at least one of preparing or initiating a dose dispensing action of the drive mechanism, and a protective member adapted to impede actuation of the dose button, wherein the protective member is releasably connected to the housing via a breakable seal.

10 Claims, 5 Drawing Sheets

(56) References Cited

U.S. PATENT DOCUMENTS

| | | |
|---|---|---|
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,324,272 A | 6/1994 | Smedley et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,056,716 A | 5/2000 | D'Antonio et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 7,854,104 B2 * | 12/2010 | Cronin .................. B65D 47/243 206/219 |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2008/0103455 A1 | 5/2008 | Domkowski et al. |
| 2009/0131864 A1 | 5/2009 | Pickhard |
| 2009/0275916 A1 | 11/2009 | Harms et al. |
| 2010/0087785 A1 | 4/2010 | Tschirren et al. |
| 2010/0087799 A1 | 4/2010 | Galbraith et al. |
| 2011/0046565 A1 * | 2/2011 | Radmer .................. A61M 5/20 604/211 |

FOREIGN PATENT DOCUMENTS

| | | |
|---|---|---|
| EP | 2246085 | 11/2010 |
| WO | 99/38554 | 8/1999 |
| WO | 01/00261 | 1/2001 |
| WO | 01/10484 | 2/2001 |

* cited by examiner

DRUG DELIVERY DEVICE WITH TAMPER-EVIDENT CLOSURE MEANS

CROSS REFERENCE TO RELATED APPLICATIONS

The present application is a U.S. National Phase Application pursuant to 35 U.S.C. §371 of International Application No. PCT/EP2012/054536 filed Mar. 15, 2012, which claims priority to European Patent Application No. 11158628.5 filed Mar. 17, 2011. The entire disclosure contents of these applications are herewith incorporated by reference into the present application.

FIELD OF THE DISCLOSURE

The present invention relates to a drug delivery device adapted to administer a dose of a medicament by way of injection. In particular, the invention refers to injection devices, such like pen-type injectors adapted to dispense a predefined dose of a medicament.

BACKGROUND

Drug delivery devices for setting and dispensing multiple doses of a liquid medicament are as such well-known in the art. Generally, such devices have substantially a similar purpose as that of an ordinary syringe.

Drug delivery devices, in particular pen-type injectors have to meet a number of user specific requirements. For instance, with patients' suffering a chronic disease e.g. diabetes, the patient may be physically infirm and may also have impaired vision. Therefore, suitable drug delivery devices need to be robust in construction and should be easy to use. Furthermore, manipulation and general handling of the device and its components should be intelligible and understandable. Moreover, a dose setting and a dose dispensing procedure must be easy to operate and unambiguous. When the device is of disposable type, it should be inexpensive to manufacture and easy to dispose. In order to meet these requirements, the number of parts and steps required to utilize the device should be kept to a minimum.

In particular, disposable devices, that are intended to be discarded after consumption of the medicament contained therein, are provided in form of a container having numerous, substantially identical drug delivery devices disposed therein. In a practical application scenario, a user may for instance be disturbed in the process of preparing the drug delivery device for a subsequent medicament dispensing procedure. In particular, the user may already have removed a protective cap from the device. When disturbed, the user may return the removable cap to its initial position and may also return the drug delivery device into the container. Upon a resumption of the dose setting and/or dispensing procedure later on, the user may no longer identify the particular drug delivery device he initially intended to use.

It is therefore an object of the present invention to provide a drug delivery device which is adapted to indicate to a user, if the device has been used before. According to another object, the device is intended to enhance patient safety and to protect the contents of the device from contamination when stored. Consequently, the invention intends to prolongate sterile conditions and the shelf life of a drug delivery device in storage.

SUMMARY

The drug delivery device according to the present invention is adapted for administering a dose of a medicament by way of injection. Preferably, the drug delivery device is designed as a pen-type injector and may be releasably coupled with a piercing assembly, e.g. with a hypodermic needle. The device comprises a housing to receive a cartridge at least partially filled with a medicament to be dispensed. The cartridge, typically comprising a pre-filled syringe, a carpule, ampoule or similar barrel-like container is sealed with a piston slidably disposed therein. The device further comprises a drive mechanism having a piston rod to be displaced in a distal direction. The piston rod is further to be operably engaged with the piston of the cartridge in order to exert distally directed pressure to the piston.

Accordingly, the piston moves in distal direction, thereby expelling a pre-defined amount of the medicament via the piercing assembly being in fluid connection with the inner volume of the cartridge.

Stepwise movement of the piston rod is controlled by the drive mechanism. The drive mechanism may be implemented all mechanically but also with electro-mechanical means for fully or semi-automated dose setting and/or dispensing.

The drug delivery device further comprises at least one actuation means being operably engaged with the drive mechanism. By way of the actuation means, a user may modify and adapt the dosage and may further initiate or even control a dose dispensing action of the drive mechanism.

Moreover, the drug delivery device comprises a protective member which is adapted to impede actuation of the actuation means when in an initial configuration. The protective member in turn is releasably connected to the housing by means of a breakable seal.

For using the drug delivery device, first of all, the protective member has to be removed or has to be at least transferred into a release configuration, thereby giving way to the actuation means. However, removal or displacement of the protective member is only possible after the breakable seal is split open or destroyed. Hence, by coupling protective member and housing by means of a breakable seal, a tamper-evident closure means can be provided for a drug delivery device inherently indicating, whether the device is used for the first time or not.

According to a preferred embodiment, the seal comprises a first ring member and a second ring member each of which being positively engaged and/or frictionally engaged with the housing and/or with the protective member, respectively. Preferably, the first ring member is mechanically engaged with the housing component whereas the second ring member is interconnected with the protective member. Upon relative displacement of protective member and housing of the drug delivery device, first and second ring members, initially interconnected with each other, may either separate from each other or at least one of first or second ring members may disintegrate.

In another embodiment, the first ring member and/or the second ring member are integrally joined or firmly bonded to the housing and/or to the protective member. It may be of further benefit, when the first ring member is positively engaged with the housing and when the second ring member is integrally joined or firmly bonded to the protective member, or vice versa.

Generally, there exist multiple variations on how to engage the first ring member with the housing and the second ring member with the protective member. In particular, by integrally joining or bonding one ring member to the protective member and by positively engaging the other ring member with the housing, a tamper-evident closure means can be effectively integrated into a mass-production process of a drug delivery device, in particular, when the protective member and/or the housing component are manufactured by way of injection moulding. Then, realization of a tamper-evident closure means can be provided even without a perforating seal member to be attached to the device, e.g. by way of an adhesive.

In a further preferred embodiment, the protective member is operably engaged with the housing. Hence, protective member and the housing comprise mutually engaging sections that provide a well-defined and controlled relative displacement of the protective member and the housing, respectively.

In a preferred embodiment, the protective member comprises a substantially cylindrical geometry. It is of particular benefit, when the protective member is threadedly engaged and/or frictionally engaged with the housing. A threaded engagement of protective member and housing allows for an easy removal or displacement of the protective member relative to the housing component. Additionally, by rotating the protective member relative to the housing, their mutual axial distance may vary, thus leading to a well-defined break-up of the breakable seal. This way, the seal does not have to be manually removed. It may disintegrate or break-up just by removing or displacing the protective member. The existence of the breakable seal does therefore not affect the general handling of the drug delivery device.

Furthermore and according to another preferred aspect, the protective member in its initial configuration almost entirely covers the actuation means, which is arranged at a proximal end section of the housing. With the protective member in its initial configuration, the actuation means is generally not accessible by the user. Dose setting or dose dispensing of the device, which is to be initiated or at least governed by the actuation means first requires to transfer the protective member into a release configuration. However, transferring the protective member into its release configuration is accompanied by a well-defined break-up of the seal.

In an alternative embodiment, the protective member comprises a central through opening at its proximal end face. The central through opening corresponds with the dimensions of the actuation means. Hence, the actuation means, typically comprising a dose button, is adapted to reach through the central through opening, when the protective member is displaced into a release configuration towards the distal direction relative to the housing.

With this embodiment, it is of further benefit, when the diameter of the central through opening of the protective member is smaller than a fingertip of an end-user. This way, depression of the actuation means is effectively impeded by the protective member as long as the actuation means does not protrude from the end face of the protective member. Typically, the diameter of the central through opening is smaller than 10 mm, preferably smaller than 8 mm and even more preferably smaller than 5 mm.

In another embodiment, the end face of protective member substantially flushes with the proximal end face of the actuation means when the protective member is in its initial configuration. Due to the comparatively small diameter of the actuation means and the corresponding through opening of the protective member, depression of the actuation means, e.g. by a fingertip of a user is generally prevented.

Only when the protective member is removed or transferred in distal direction into a release configuration, in which the actuation means protrudes through the central through opening of the protective member, appropriate usage of the device is enabled.

In still another embodiment, the first ring member comprises a number of ring segments that are interconnected by predetermined breaking points or breaking sections. Each one of the ring segments of the first ring member are individually connected to the second ring member. During a break-up or a split open of the seal, the first ring member may disintegrate into a number of ring segments, each of which remain connected to the second ring member.

This way, break-up of the seal does not produce any detached or separated pieces. Hence, no additional waste or garbage is produced. Moreover, by interconnecting the ring segments of the first ring member with the second ring member, a force effect originating from mutual displacement of protective member and housing may transfer to the second ring member. As soon as a pre-defined separation force is exceeded, the numerous ring segments may separate from each other along the predetermined breaking points or sections.

According to a further preferred embodiment, the first ring member disintegrates into the ring segments along the predetermined breaking points when it becomes subject to a radially and/or axially directed force effect.

Moreover, it is intended, that the actuation means comprises an actuation button or dose button adapted to be depressed by a user in distal direction for dispensing and/or for setting of a dose of the medicament.

The dose button may also comprise a cylindrical sleeve. It may be subject to rotation and/or axial displacement relative to the housing.

Moreover, the drug delivery device is preferably of disposable type and comprises a pre-filled cartridge (e.g. a carpule or a pre-filled syringe) disposed in the housing, preferably in a cartridge holder section of the housing. When after a single or several dose setting and dose dispensing procedures the medicament contained in the cartridge is used up, the entire drug delivery device might be intended to be discarded.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

Moreover, even though the invention is illustrated by way of a pen-type injector, it is by no way limited to such devices. In the present context, a drug delivery device can be designed as a multi-dose pen-type injector as a well as single-dose and/or auto-injector. Also, safety syringes and injector systems allowing for fixed and/or variable dosage can be implemented with the described tamper-evident closure means.

BRIEF DESCRIPTION OF THE DRAWINGS

In the following preferred embodiments of the invention will be described in greater detail by making reference to the drawings, in which.

DETAILED DESCRIPTION

Figure 1:
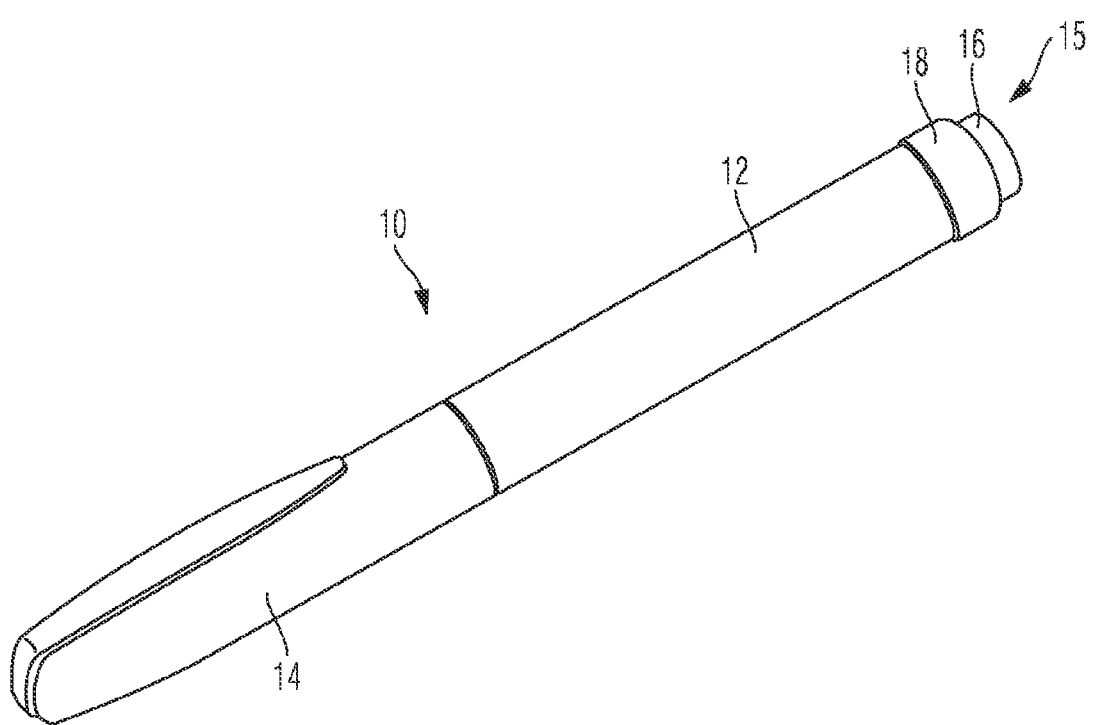
FIG. 1 schematically illustrates the outer appearance of a drug delivery device.

FIG. 1 schematically illustrates a drug delivery device 10 designed as a pen-type injector. The device 10 comprises a proximal housing component 12 as well as a distal housing component 14, the latter of which being releasably connected to the housing 12, either directly or by way of a cartridge holder section adapted to receive a cartridge comprising the medicament to be dispensed by the drug delivery device 10. Typically, the protective cap 14 protects the cartridge holder section, which is typically to be releasably connected with a needle assembly providing a fluid connection between the inner volume of the cartridge and biological tissue to be treated with said medicament.

The proximal housing section 12 typically comprises a drive mechanism not further illustrated here. The drive mechanism comprises a displaceable piston rod to be operably engaged with a piston of the cartridge in order to expel a pre-defined amount of the liquid medicament from the cartridge. Dose setting and/or dose dispensing can be controlled by way of an actuation means 16 positioned at a proximal end section 15 of the drug delivery device 10.

Figure 2:
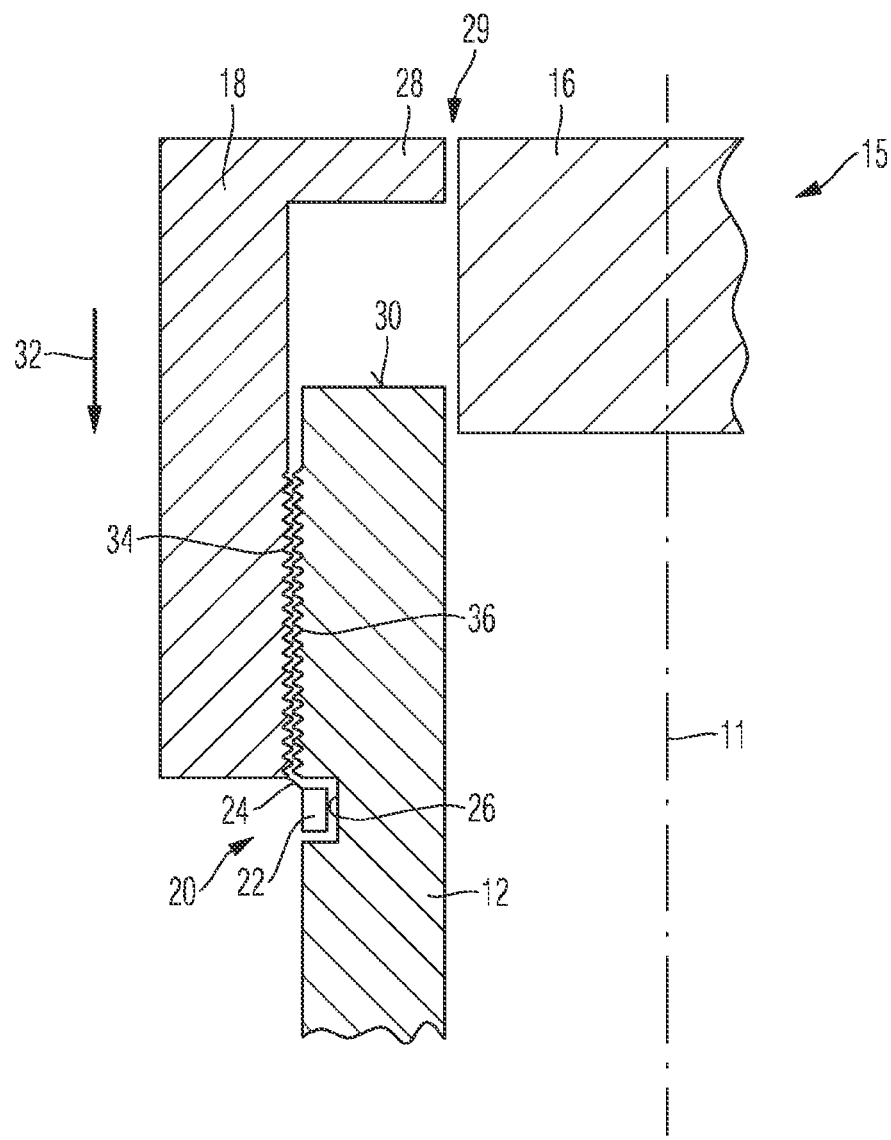
FIG. 2 shows a cross section of a proximal end of the drug delivery device provided with a protective member according to a first embodiment.

As indicated in FIGS. 1 and 2, the actuation means is surrounded and enclosed by a sleeve-like protective member 18. As illustrated in FIG. 2 in detail, the protective member 18 is threadedly engaged with the distal portion of the housing 12 by way of mutually corresponding threaded sections 34, 36. Moreover, in its initial configuration as depicted in FIG. 2, the sleeve-like protective member 18 comprises a radially inwardly directed flange portion 28 at its proximal end face which substantially flushes with a proximal end face of the actuation means 15, which, in the present embodiment comprises a dose button 16, that is adapted to be depressed in distal direction 32.

In other words, the protective member 18 comprises a central through opening 29 with respect to a central axis 11. The size of the through opening 29 matches with the radial dimensions of the dose button 16.

When transferring the protective member 18 in distal direction 32 towards a release configuration, which is indicated in FIG. 1, the actuation means 16 may protrude from the protective member 18. In such release configuration, the dose button 16 may be ready to be rotated or depressed according to the particular mechanical implementation of the drive mechanism.

As further illustrated in FIG. 2, the seal 20 comprises at least a first ring member 22 positively engaged with the housing component 12. The ring member 22 is arranged in a circumferential recess or groove 26. Moreover, the first ring member 22 is integrally formed with the cylindrical sleeve of the protective member 18, which serves as a second ring member. First and second ring members 22, 18 are integrally formed by way of structurally weakened interconnecting portion 24.

As soon as the protective member 18, hence the second ring member, is rotated with respect to the housing 12 it may experience a downward directed axial displacement in distal direction. As a consequence, the structurally weakened interconnection portion 24 may tear apart and the cylindrical portion 18 of the protective member may cover the first ring member 22, which stays in the circumferential recess 26. Even in case that the protective member 18 is returned to its initial configuration as illustrated in FIG. 2, an end-user may observe the broken seal 20, thus indicating, that the drug delivery device has already been in use.

A distally directed displacement of the protective member 18 relative to the housing component 12 is stopped when the radially inwardly extending flange portion 28 of the protective member 18 gets in contact with the proximal end face 30 of the housing component 12, which serves as a stop face. When getting in contact with the stop face 30, the protective element 18 is still threadedly engaged with the housing component 12 and may therefore remain attached thereto.

Figure 3:
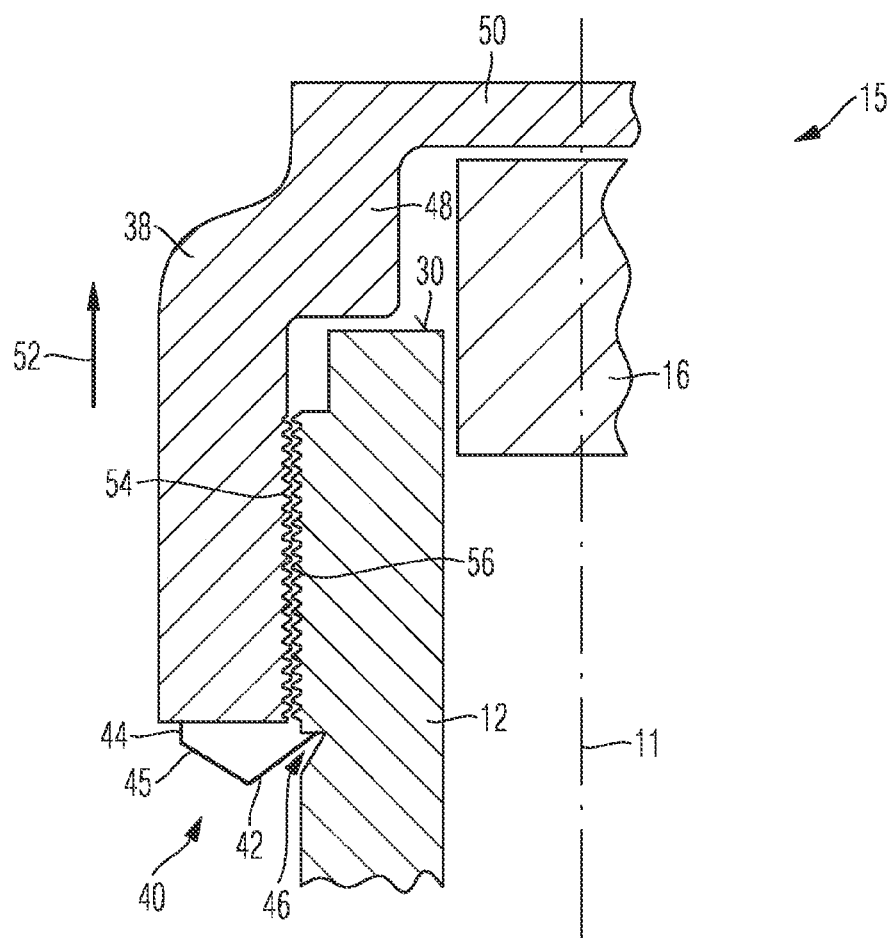
FIG. 3 shows another embodiment of a protective member releasably attached to the proximal end of the drug delivery device

FIG. 3 illustrates an alternative embodiment, wherein a protective cap 38 is also threadedly engaged with a proximal end section of a housing 12 by way of mutually corresponding threads 54, 56. Here, the protective member 38 comprises a radially inwardly pointing shoulder portion 48 which is adapted to but against a proximal end face of the housing 12. The protective member 38 comprises a cupped geometry and has a closed bottom structure 50 entirely covering the actuation means 16 disposed underneath.

In contrast to the embodiment according to FIG. 2, the protective member 38 is intended to be removed from the housing 12 by initiating an unscrewing motion.

Hence, the protective member 38 is intended to be displaced in proximal direction 52 in order to give access to the dose button 16. The protective member 38 is mechanically engaged with the housing 12 by way another type of seal 40 being separately illustrated in FIG. 4.

Figure 4:
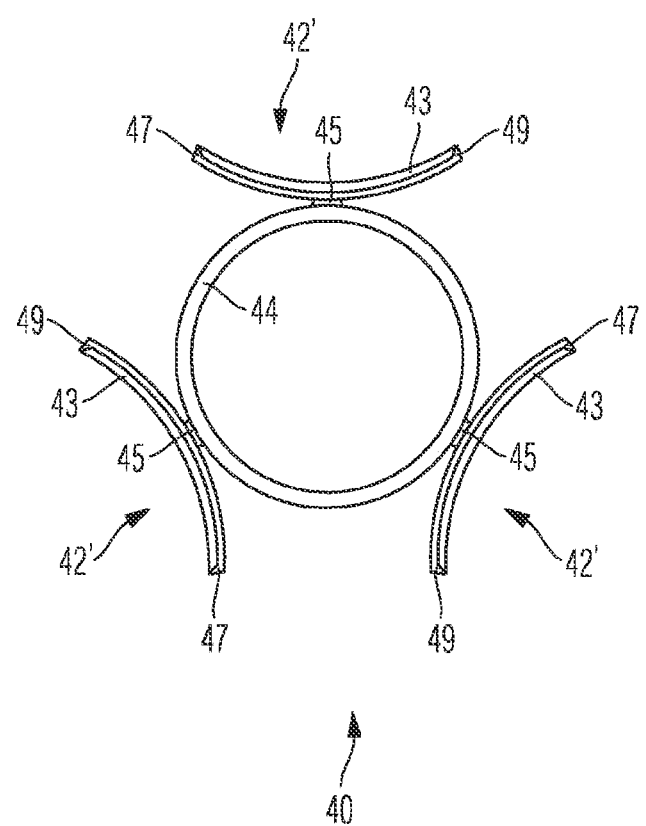
FIG. 4 depicts a breakable seal as used in the embodiment according to FIG. 3 in an isolated perspective illustration.
Figure 5:
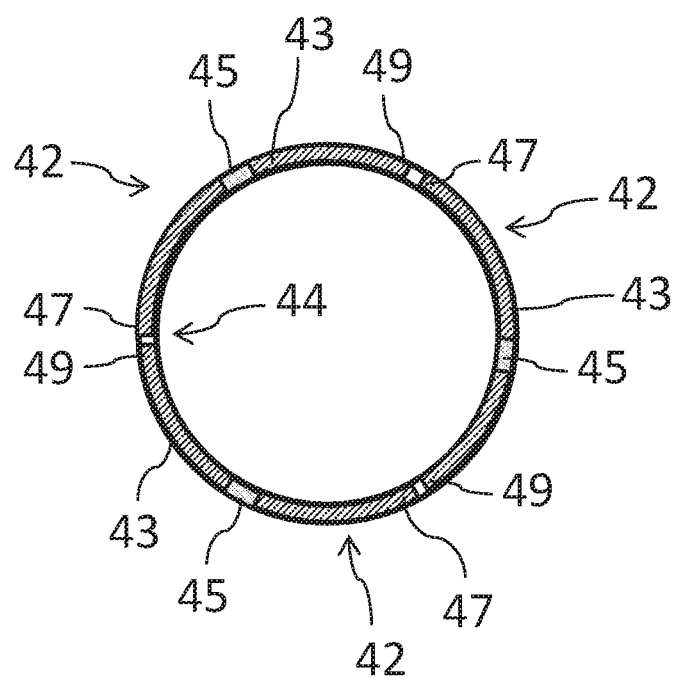
FIG. 5 depicts the breakable seal of FIG. 4 in an initial configuration where the first ring member and the second ring member are concentrically arranged with respect to each other and sharing a center.

The seal 40 comprises a first ring member 42 and a second ring member 44. In the embodiment according to FIG. 3, the second ring member 44 is integrally formed or positively engaged with a distal end section of the sleeve-like protective member 38. The second ring member 42 in turn is positively engaged with the housing component 12. As illustrated in FIG. 4, the first ring member 42' shown in a split-open configuration comprises three ring segments 43, which in an initial configuration are interconnected with their end sections 47, 49 facing towards each other. Each of the segments 43 of the first ring member 42' is individually connected to the second ring member 44 by a joint 45.

As indicated in FIGS. 3 and 4, the ring segments 43 comprise a somewhat triangular but open shape. With their free end section facing radially inwardly and in proximal direction 52, the ring segments 43 of the first ring member 42 positively engage with a groove or recess 46 provided at the outer circumference of the housing 12. In particular, the recess is designed as a kind of undercut 46.

When the protective sleeve 38 is displaced in proximal direction 52 relative to the housing 12, a respective proximally directed force effect is transferred to the second ring member 44 and to the first ring member 42. As soon as the applied force exceeds a predefined threshold, predetermined breaking points or perforated and weakened structures interconnecting the three ring segments 43 of the first ring member 42 will start to tear apart the first ring member 42. Once the first ring member 42 is disintegrated into the various ring segments 43 as illustrated in FIG. 4, a clear indication is given, that the drug delivery device has been used.

The invention claimed is:

1. A drug delivery device for administering a dose of a medicament by way of injection, the device comprising:
    a housing to receive a cartridge at least partially filled with a medicament and being sealed with a piston slidably disposed therein,
    a drive mechanism having a piston rod to be displaced in a distal direction to operably engage with the piston of the cartridge,
    a dose button operably engaged with the drive mechanism for at least one of preparing and initiating a dose dispensing action of the drive mechanism, and
    a protective member adapted to impede actuation of the dose button, wherein the protective member is releasably connected to the housing via a breakable seal, and wherein the protective member comprises a threaded section that mates with a threaded section of the housing such that the protective member is threadedly engaged with the housing in at least an initial configuration,
    wherein the seal comprises a first ring member and a second ring member, wherein the first ring member is positively engaged or frictionally engaged, integrally joined or firmly bonded to the housing in the initial configuration and the second ring member is positively engaged or frictionally engaged, integrally joined or firmly bonded to the protective member such that the first ring member and the second ring member are concentrically arranged with respect to each other, sharing a center in the initial configuration, and wherein the first ring member comprises a number of ring segments interconnected by predetermined breaking points and being individually connected to the second ring member, and wherein the first ring member disintegrates into the ring segments along the predetermined breaking points when the first ring member becomes subject to at least one of a radially directed force effect and an axially directed force effect.

2. The drug delivery device according to claim 1, wherein the first ring member is positively engaged with the housing and wherein the second ring member is integrally joined or firmly bonded to the protective member.

3. The drug delivery device according to claim 1, wherein the protective member is operably engaged with the housing.

4. The drug delivery device according to claim 3, wherein the protective member comprises a substantially cylindrical geometry.

5. The drug delivery device according to claim 3, wherein the protective member entirely covers the dose button arranged at a proximal end section of the housing in the initial configuration.

6. The drug delivery device according to claim 3, wherein a proximal end face of the protective member comprises a central through opening adapted to receive the dose button when the protective member is displaced into a release configuration in the distal direction relative to the housing.

7. The drug delivery device according to claim 6, wherein the diameter of the central through opening of the protective member is smaller than 10 mm.

8. The drug delivery device according to claim 6, wherein the proximal end face of the protective member flushes with a proximal end face of the dose button when in the initial configuration.

9. The drug delivery device according to claim 1, wherein the dose button is adapted to be depressed in the distal direction for dispensing of a dose of the medicament.

10. The drug delivery device according to claim 1, further comprising a pre-filled cartridge disposed therein.

* * * * *